United States Patent [19]
Yang

[11] Patent Number: 5,401,240
[45] Date of Patent: Mar. 28, 1995

[54] VAGINA CLEANING DEVICE

[76] Inventor: Chin-Wen Yang, P.O. Box 65-76, Taichung, Taiwan, Prov. of China

[21] Appl. No.: 238,525

[22] Filed: May 5, 1994

[51] Int. Cl.⁶ .............................................. A61M 3/02
[52] U.S. Cl. .................................... 604/39; 604/40
[58] Field of Search ............... 604/36, 37, 38, 39–43, 604/212–219

[56] References Cited

U.S. PATENT DOCUMENTS

| | | | |
|---|---|---|---|
| 1,082,142 | 12/1913 | Spardel | 604/39 |
| 1,526,313 | 2/1925 | Blakeslee | 604/39 |
| 1,779,268 | 10/1930 | Belfrage | 604/39 |
| 1,845,343 | 2/1932 | Salerni | 604/39 |
| 2,147,652 | 2/1939 | Kennison | 604/39 |
| 2,265,080 | 12/1941 | Mezey | 604/39 |
| 2,421,294 | 5/1947 | Shotton | 604/39 |
| 2,576,766 | 11/1951 | Sokolik | 604/39 |

*Primary Examiner*—Michael A. Brown

[57] ABSTRACT

A device for cleaning vagina includes a housing, a spout is engaged with the housing for inserting into vagina and for guiding water into the vagina, a number of outflow passages are formed in the spout for allowing water to flow out of the vagina, and a valve is engaged in the housing for controlling water flowing through the housing and flowing into the spout, water may be injected into vagina for cleaning purposes and may flow out via the outflow passages.

1 Claim, 4 Drawing Sheets

VAGINA CLEANING DEVICE

BACKGROUND OF THE INVENTION

1. Field of the Invention

The present invention relates to a cleaning device, and more particularly to a vagina cleaning device.

2. Description of the Prior Art

Typically, for contraception purposes, contraceptives, such as contraceptive jelly, intrauterine contraceptive rings are required to be applied or inserted through vagina and disposed in the interior of women body. This is inconvenient.

In order to avoid the inconvenience, some people simply use the shower nozzle to clean vagina in order for contraceptive purposes, however, vagina can not be thoroughly cleaned with shower nozzle.

The present invention has arisen to mitigate and/or obviate the afore-described disadvantages of the conventional contraceptives.

SUMMARY OF THE INVENTION

The primary objective of the present invention is to provide a cleaning device for thoroughly cleaning vagina of women bodies.

In accordance with one aspect of the invention, there is provided a device for cleaning vagina comprising a housing including a bore formed therein and including a first end and a second end, an annular flange formed in the bore, a spout engaged with the first end of the housing for inserting into vagina and for guiding water into the vagina, outflow passage means formed in the spout for allowing water to flow out of the vagina, and a valve means disposed in the bore for controlling water flowing to the spout, the valve means including a tube slidably engaged in the bore and having a first end having a head formed thereon for engaging with the housing and for enclosing the bore, the tube including a second end having an outer thread formed thereon, a plurality of openings formed in the tube for allowing water to flow into the spout from the tube, wedge means formed on the tube for engaging with the annular flange of the housing so as to actuate the head to enclose the bore, a barrel including an inner thread formed therein for engaging with the outer thread of the tube, means biased between the barrel and the tube for biasing the head to enclose the bore, and means for coupling the tube to water reservoir, the openings being opened when the head is disengaged from the housing, the head being forced against the biasing means in order to open the bore when the openings are opened, whereby, water is allowed to flow into the vagina for cleaning purposes and is allowed to flow out via the outflow passage means.

Further objectives and advantages of the present invention will become apparent from a careful reading of a detailed description provided hereinbelow, with appropriate reference to accompanying drawings.

DETAILED DESCRIPTION OF THE PREFERRED EMBODIMENT

Figure 1:
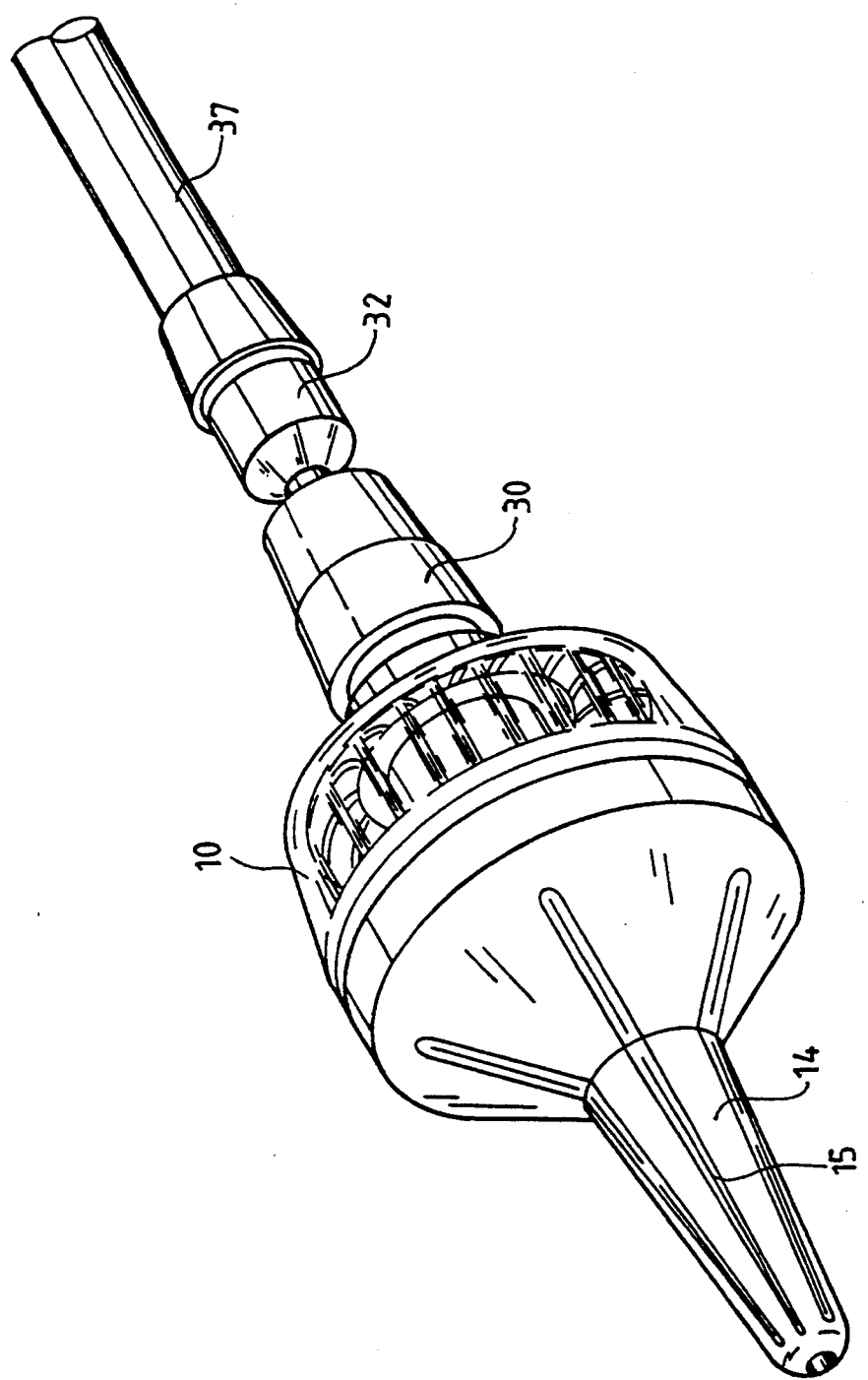
FIG. 1 is a perspective view of a vagina cleaning device in accordance with the present invention.
Figure 2:
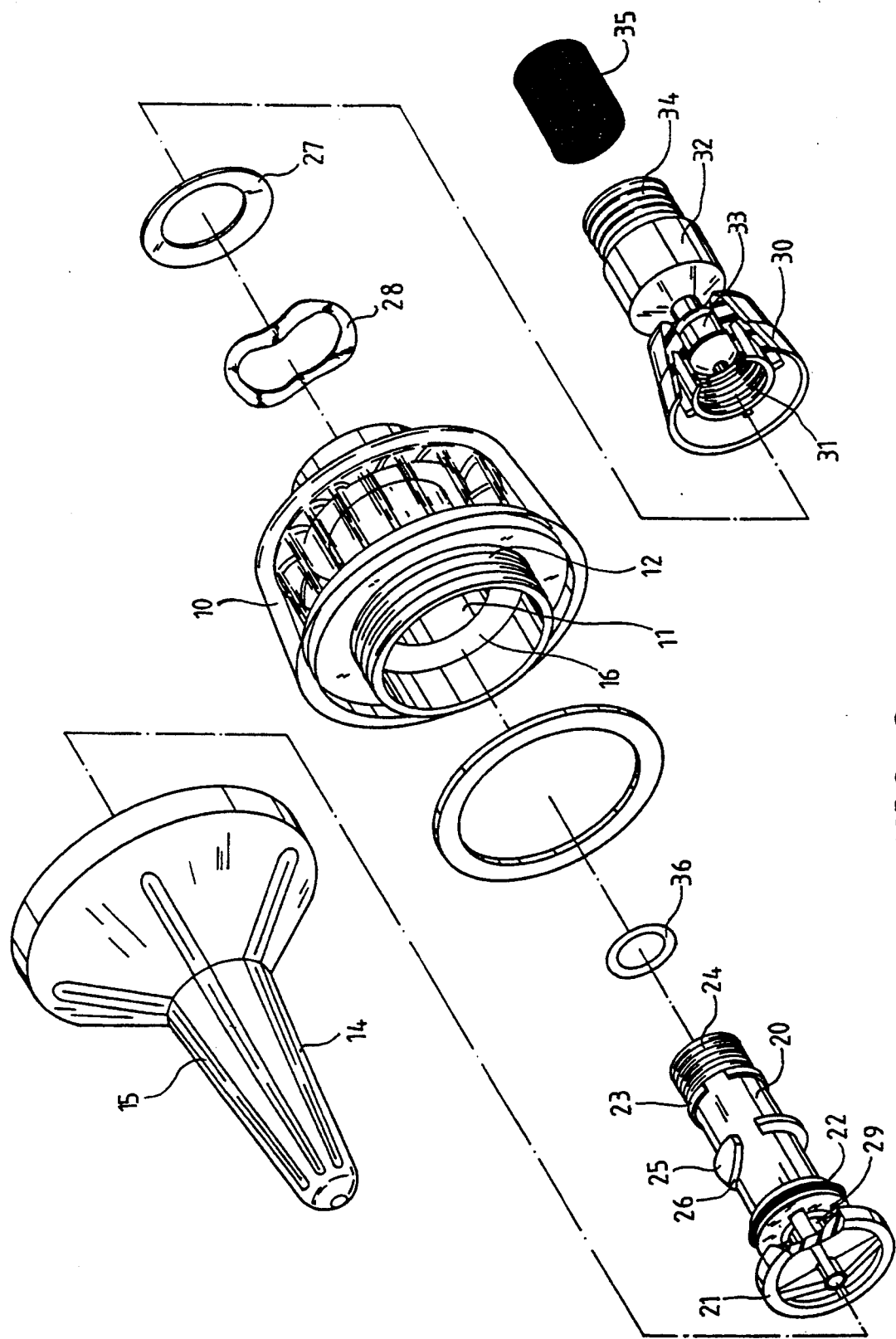
FIG. 2 is an exploded view of the vagina cleaning device.
Figure 3:
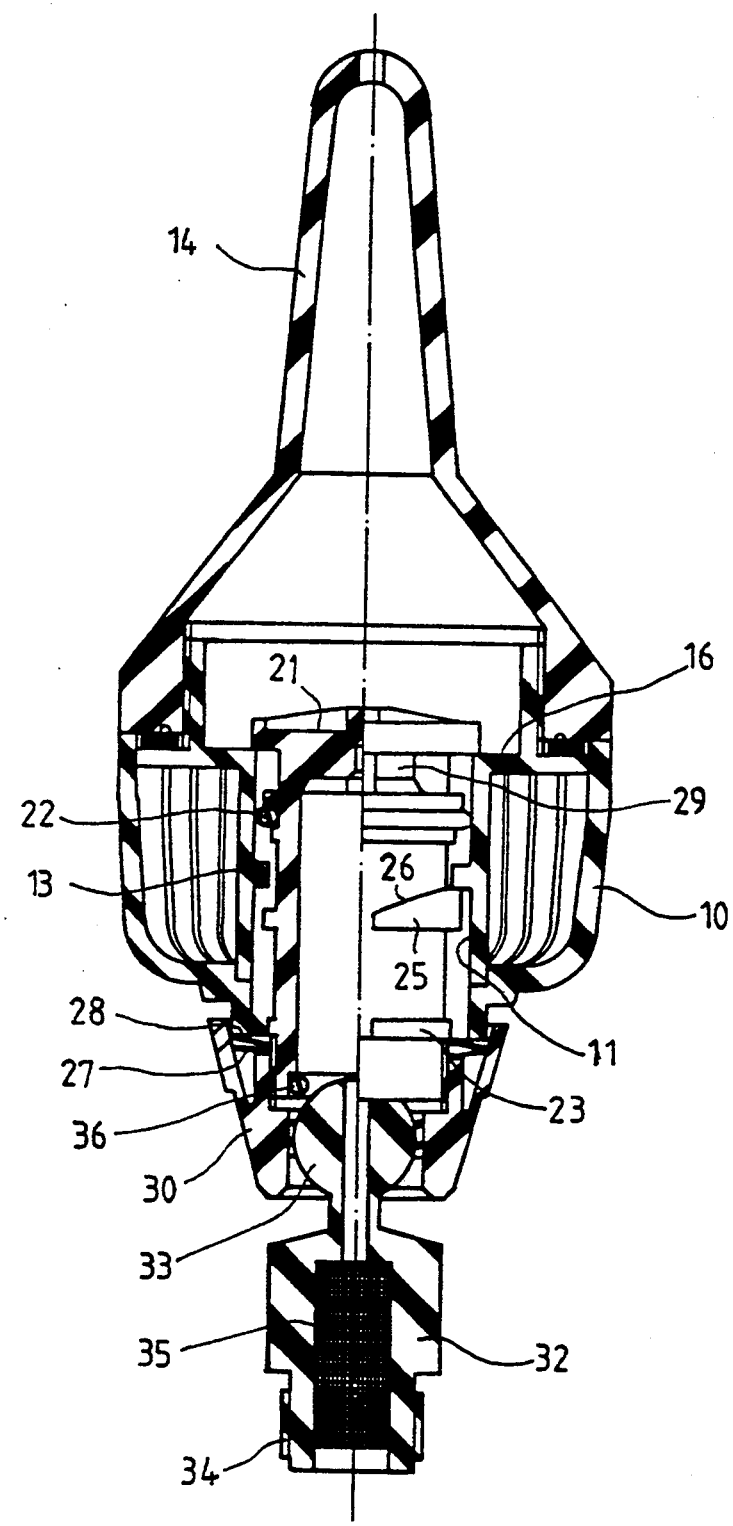
FIGS. 3 and 4 are cross sectional views illustrating the operation of the vagina cleaning device.

Referring to the drawings, and initially to FIGS. 1 to 3, a vagina cleaning device in accordance with the present invention comprises a housing 10 including a bore 11 formed therein, an outer thread 12 and a shoulder 16 formed in one end of the housing 10, and an annular flange 13 formed in the bore 11 of the housing 10, a spout 14 threadedly engaging with the outer thread 12 of the housing 10 for inserting into the vagina and having a number of grooves 15 longitudinally formed in the outer peripheral surface thereof, a tube 20 slidably engaged in the bore 11 of the housing 10 and including a head 21 formed on one end for engaging with the shoulder 16 of the housing 10 for enclosing the bore 11, a sealing ring 22 engaged between the tube 20 and the housing 10 for making a water tight seal therebetween, a number of openings 29 formed in the tube 20, close to the head 21 for allowing water to flow into the spout 14 from the interior of the tube 20, an annular flange 23 and an outer thread 24 formed on the other end of the tube 20, a wedge 25 formed in the outer peripheral surface of the tube 20 and including a tapered surface 26 formed thereon for engaging with the annular flange 13, a barrel 30 including an inner thread 31 for engaging with the outer thread 24 of the tube 20, a washer 27 and a spring element 28 engaged between the barrel 30 and the tube 20 and engaged with the annular flange 23 of the tube 20, a coupler 32 including a ball-shaped head 33 formed on one end for rotatably engaging in the barrel 30 and an outer thread 34 formed on the other end for coupling to a reservoir by a hose 37 or the like, a filtering member 35 engaged in the coupler 32 for filtering the water flowing through the coupler 32, and a sealing ring 36 engaged between the head 33 and the tube 20 for making a water-tight seal therebetween.

In operation, as shown in FIG. 3, the bore 11 of the housing 10 is enclosed by the head 21 of the tube 20 when the tapered surface 26 of the wedge 25 is engaged with the annular flange 13, at this moment, the water from the coupler 32 is blocked and may not flow through the spout 14.

Figure 4:
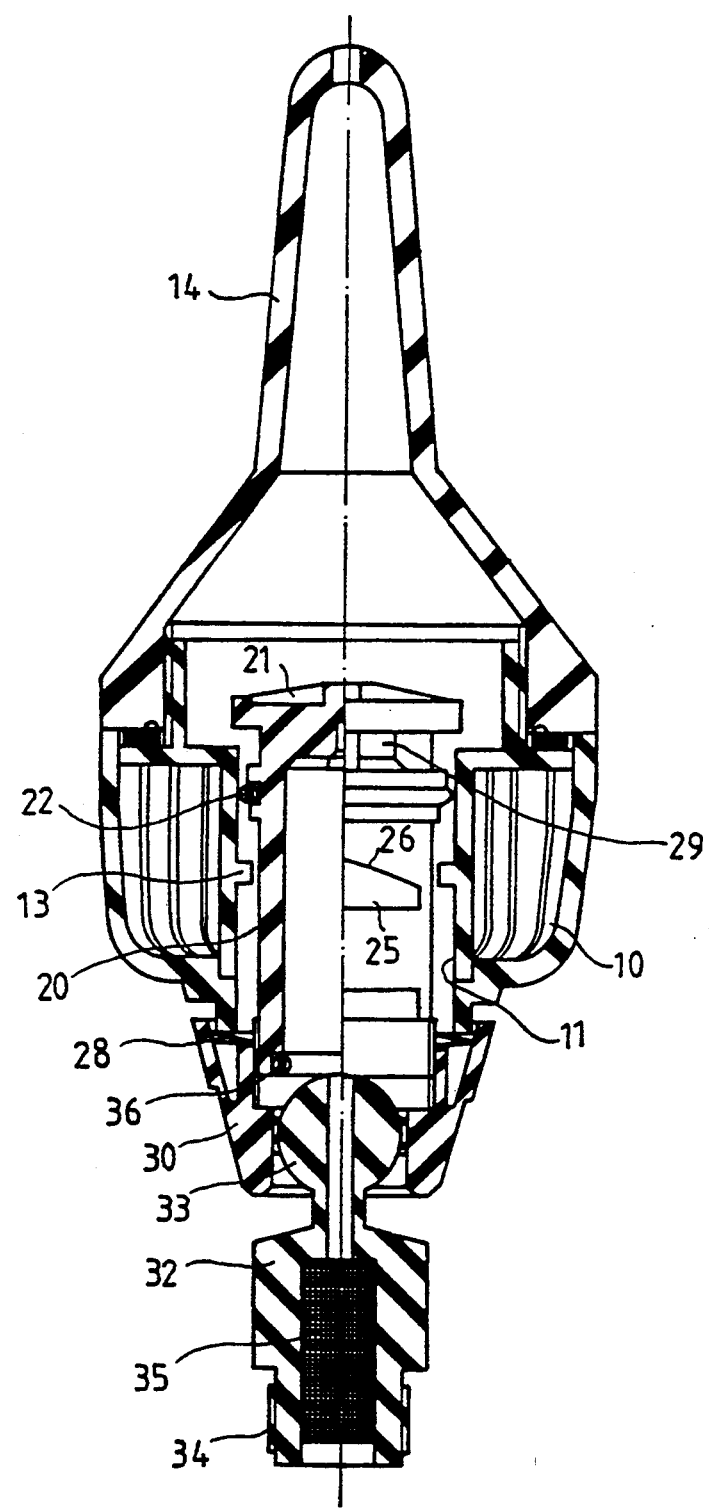

When the barrel 30 is rotated relative to the tube 20, the openings 29 may be gradually opened by the engagement between the tapered surface 26 and the annular flange 13, as shown in FIG. 4, the head 21 of the tube 20 may be disengaged from the annular shoulder 16 of the housing such that water from the coupler 32 may flow into the spout 14 via the openings 29. It is to be noted that the water flowing into the tube 20 from the coupler 32 may apply a force against the head 21 of the tube 20 such that the head 21 may be pushed toward the spout 14 against the spring member 28 and such that the openings 29 may widely opened, whereby, water may flow into the spout 14 and may flow out of the spout 14 via the openings 29.

It is further to be noted that water flowing into the vagina for cleaning purposes may flow out of the vagina via the outflow passages, i.e., the grooves 15.

Accordingly, vagina may be easily cleaned by the cleaning device in accordance with the present invention.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A device of cleaning vagina comprising a housing including a bore formed therein and including a first end and a second end, an annular flange formed in said bore, a spout engaged with said first end of said housing for inserting into vagina and for guiding water into said vagina, outflow passage means formed in said spout for allowing water to flow out of said vagina, a tube slidably engaged in said bore and including a first end having a head formed thereon for engaging with said housing and for enclosing said bore, said tube including a second end having an outer thread formed thereon, a plurality of openings formed in said tube for allowing water to flow into said spout from said tube, wedge means formed on said tube for engaging with said annular flange of said housing so as to actuate said head to enclose said bore, a barrel including an inner thread formed therein for engaging with said outer thread of said tube, means biased between said barrel and said tube for biasing said head to enclose said bore, and means for coupling said tube to water reservoir, said openings being opened when said head is disengaged from said housing, said head being forced against said biasing means in order to open said bore when said openings are opened, whereby, water is allowed to flow into said vagina for cleaning purposes and is allowed to flow out via said outflow passage means.

* * * * *